US012496107B2

(12) United States Patent
Zander et al.

(10) Patent No.: US 12,496,107 B2
(45) Date of Patent: Dec. 16, 2025

(54) FRACTURE FIXATION SYSTEM

(71) Applicant: Stryker European Operations Limited, Carrigtwohill (IE)

(72) Inventors: Nils Zander, Eckernförde (DE); Manfred Wieland, Kiel (DE); Bernd Simon, Kiel (DE); James Durham, Cork (IE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/838,393

(22) PCT Filed: Feb. 15, 2023

(86) PCT No.: PCT/IB2023/000070
§ 371 (c)(1),
(2) Date: Aug. 14, 2024

(87) PCT Pub. No.: WO2023/156848
PCT Pub. Date: Aug. 24, 2023

(65) Prior Publication Data

US 2025/0152214 A1 May 15, 2025

Related U.S. Application Data

(60) Provisional application No. 63/310,328, filed on Feb. 15, 2022.

(51) Int. Cl.

| | |
|---|---|
| ***A61B 17/74*** | (2006.01) |
| ***A61B 90/00*** | (2016.01) |
| *A61B 17/00* | (2006.01) |

(52) U.S. Cl.
CPC ............ *A61B 17/746* (2013.01); *A61B 90/03* (2016.02); *A61B 2017/00477* (2013.01); *A61B 2090/034* (2016.02)

(58) Field of Classification Search
CPC ............. A61B 90/03; A61B 2090/034; A61B 2017/00477
See application file for complete search history.

(56) References Cited

U.S. PATENT DOCUMENTS

| | | |
|---|---|---|
| 5,429,641 A | 7/1995 | Gotfried |
| 7,135,023 B2 | 11/2006 | Watkins et al. |

(Continued)

FOREIGN PATENT DOCUMENTS

| | | |
|---|---|---|
| CN | 104873262 A | 9/2015 |
| WO | 2007/109302 A2 | 9/2007 |

OTHER PUBLICATIONS

Fixation using Alternative Implants for the Treatment of Hip fractures (FAITH) Investigators. "Fracture fixation in the operative management of hip fractures (FAITH): an international, multicentre, randomised controlled trial." Lancet (London, England) vol. 389, 10078 (Apr. 2017): 1519-1527. doi:10.1016/S0140-6736(17)30066-1.

(Continued)

*Primary Examiner* — Sameh R Boles
(74) *Attorney, Agent, or Firm* — Lerner David LLP

(57) ABSTRACT

A fracture fixation system includes a fixation element and a peg. The fixation element has a plate and a barrel, the plate having an outer surface and an inner surface for placement against an exterior surface of a bone, and the barrel extending along a barrel axis and having a peripheral wall protruding from the inner surface of the plate, the fixation element defining a passage through the plate and the barrel that extends along the barrel axis, wherein at least a portion of an inner surface of the peripheral wall of the barrel has a figure-8 shape in a plane perpendicular to the barrel axis. The monolithic peg extends along a peg axis and is configured for insertion into the passage, wherein a body of the peg (Continued)

has an outer surface defining a figure-8 shape in a plane perpendicular to the peg axis.

20 Claims, 13 Drawing Sheets

(56) References Cited

U.S. PATENT DOCUMENTS

| | | | |
|---|---|---|---|
| 7,780,667 | B2 | 8/2010 | Watanabe et al. |
| 7,799,030 | B2 | 9/2010 | Watanabe et al. |
| 7,918,853 | B2 | 4/2011 | Watanabe et al. |
| 7,931,652 | B2 | 4/2011 | Ferrante et al. |
| 8,398,636 | B2 | 3/2013 | Simon et al. |
| 8,734,494 | B2 | 5/2014 | Simon et al. |
| 8,939,978 | B2 | 1/2015 | Watanabe et al. |
| 2005/0055024 | A1 | 3/2005 | James et al. |
| 2008/0262498 | A1* | 10/2008 | Fernandez Dell'Oca .................. A61B 17/744 606/65 |

OTHER PUBLICATIONS

International Search Report and Written Opinion issued in Appln. No. PCT/IB2023/000070 mailed Aug. 4, 2023 (18 pages).
Smith & Nephew, "TRIGEN INTERTAN Intertrochanteric Antegrade Nail". Orthopaedics Smith & Nephew, Inc., (Feb. 2012). 48 pgs.

* cited by examiner

FRACTURE FIXATION SYSTEM

CROSS-REFERENCE TO RELATED APPLICATIONS

The present application is a national phase entry under 35 U.S.C. § 371 of International Application No. PCT/IB2023/000070, filed Feb. 15, 2023, published in English, which claims the benefit of the filing date of U.S. Provisional Application No. 63/310,328, filed Feb. 15, 2022, the disclosures of which are hereby incorporated herein by reference.

BACKGROUND OF THE INVENTION

The present invention relates to orthopedic surgical devices used to join and promote healing of fractured bone, and more particularly, and not by limitation, devices used to fixate proximal femoral fractures.

The surgical treatment of femoral neck fractures utilizing internal fixation remains challenging, especially for dislocated unstable fractures. There are a variety of devices used to treat fractures of the femur, humerus, tibia, and other long bones. For example, fractures of the femoral neck, head, and intertrochanteric region have been successfully treated with a variety of internal fixation means such as compression screw assemblies, which may include a plate having a barrel, a lag screw, and a compressing screw. Compression hip and bone screw devices for use in fixating a fractured bone during the healing process have been used for years. It is mainstream practice for surgeons to utilize cannulated compression screws (CCS) or short head screws (SHS) as compression screws in internal fixation systems.

For many surgeons and customers, the utilization of CCS or SHS devices remain the treatment of choice. However, CCS and SHS account for nearly 30% of hip fracture failures and their disadvantages are well documented. In particular, CCS devices are not angularly stable, have insufficient rotation control, and suffer from uncontrolled shortening of the femoral neck and limited resistance against shear forces. The disadvantages of SHS are that an additional anti-rotation screw is required with limited space particularly in small anatomies, that they have large lateral footprints, and also that they create a potential collision with a retrograde nail in the case of ipsilateral neck-shaft fixation.

Additionally, problems may result from weakened or poor-quality bone that is adjacent to the fracture site. Often times the bone adjacent to the fracture is weak and is prone to damage when exposed to compression. For example, there could be uncontrolled shortening of the femoral head when the femoral head compresses towards or into the fracture site. In extreme cases, uncontrolled shortening may cause the femoral head to be compressed all the way into the trochanteric region of the femur.

Thus, it would be desirable to provide a fracture fixation system to improve on the prior art disadvantages.

BRIEF SUMMARY OF THE INVENTION

A first aspect of the present invention is a fracture fixation system for securing a fractured femoral neck to the femoral shaft and includes a fixation element including a plate and a barrel. The plate has an inner surface for placement against an exterior surface of the bone, and the barrel extends along a barrel axis and has a peripheral wall protruding from the inner surface of the plate. The fixation element defines a passage through the plate and the barrel that extends along the barrel axis, wherein at least a portion of an inner surface of the peripheral wall of the barrel has a figure-8 shape in a plane perpendicular to the barrel axis. Also, a monolithic peg extends along a peg axis and is configured for insertion into the passage, wherein a body of the peg has an outer surface defining the figure-8 shape in a plane perpendicular to the peg axis.

In accordance with other embodiments of the first aspect, the peg may be comprised of overlapped cylindrical portions that define the figure-8 shape of the outer surface of the peg. The overlapped cylindrical portions may include a larger cylindrical portion defined by a larger radius and a smaller cylindrical portion defined by a smaller radius. Each of the larger and smaller cylindrical portions of the peg may define a lumen. The lumen of the smaller cylindrical portion may have a diameter that is larger than a diameter of the lumen of the larger cylindrical portion. The cylindrical portions of the peg may have different maximum lengths along the peg axis. The larger and smaller cylindrical portions of the peg may have different maximum lengths along the peg axis, and the length of the smaller cylindrical portion of the peg may be shorter than the length of the larger cylindrical portion of the peg. The figure-8 shape of the peripheral wall of the barrel and the figure-8 shape of the outer surface of the peg may be substantially similar in size and shape.

A portion of the peripheral wall of the barrel may define a spring arm with a hook facing toward an internal space of the barrel. A groove of the peg in an outer surface of the peg and configured for engagement with the hook may extend only along a portion of a length of the peg and may define an end wall, such that the hook limits movement of the peg within the passage when the hook contacts the end wall.

Separate portions of the peripheral wall of the barrel may define respective first and second spring arms each having a hook. A first groove in an outer surface of the peg and configured for engagement with the first hook may extend from a first end of the peg only along a portion of a length of the peg and define a first end wall, such that the hook of the first arm limits movement of the peg within the passage when the first hook contacts the first end wall, and a second groove in the outer surface of the peg and configured for engagement with the second hook may extend from a second end of the peg opposite the first end of the peg only along a portion of the length of the peg and define a second end wall, such that the hook of the second arm limits movement of the peg within the passage when the second hook contacts the second end wall. The first end wall and the second end wall may be misaligned along the peg axis. The second end of the peg may be disposed closer to the plate than the first end of the peg when the peg is at least partially disposed within the passage of the fixation element, and a floor of the second groove may be tapered to be shallower at the second end wall, and a floor of the first groove may be at a substantially constant depth along an entire length of the first groove.

The peripheral wall of the barrel may be nearer to a first end of the plate than to an opposed second end of the plate, the second end may have a perimeter with a dovetail shape. The plate may include left and right sides each extending from the first end to the second end, and the second end may include one hole on the left side and one hole on the right side.

The peripheral wall of the barrel may be nearer to a first end of the plate than to an opposed second end of the plate, the inner surface of the peripheral wall may be defined by overlapped cylindrical surface that define the figure-8 shape of the inner surface, and a larger cylindrical surface of the overlapped cylindrical portions may be nearer to the first end of the plate than to the second end of the plate. The peg may be at least partially disposed within the passage of the fixation element, the peg may be comprised of overlapped cylindrical portions that define the figure-8 shape of the outer surface of the peg, the overlapped cylindrical portions may include a larger cylindrical portion defined by a larger radius and a smaller cylindrical portion defined by a smaller radius, each of the larger and smaller cylindrical portions of the peg defining a lumen, and a threaded lag screw may be disposed through the lumen of the smaller cylindrical portion of the peg. The second end of the plate may define two screw holes, and two threaded fixation screws may be disposed through the two screw holes, respectively. The fracture fixation system may further include a threaded lag screw for insertion within a lumen of the peg, and a threaded fixation screw for insertion through a screw hole at the second end of the plate.

The fracture fixation system may further include a threaded lag screw for insertion within a first lumen of the peg, and a threaded fixation screw for insertion through a screw hole at an end of the plate. The fracture fixation system may further include a positioning screw for insertion within a second lumen of the peg. The fracture fixation system may further include a collar having an outer surface for engagement with an inner surface of the second lumen of the peg, and an inner surface for engagement with a shaft of the positioning screw. The outer surface of the collar and the inner surface of the second lumen of the peg may be non-circular, and the inner surface of the collar and the shaft of the positioning screw may be threaded. The lag screw may be comprised of distinct proximal and distal components that are assembled together within the first lumen.

A second aspect of the present invention is a fracture fixation system, including a fixation element including a plate and a barrel, the plate having an inner surface for placement against an exterior surface of a bone, and the barrel extending along a barrel axis and having a peripheral wall protruding from the inner surface of the plate, the fixation element defining a passage through the plate and the barrel that extends along the barrel axis, wherein at least a portion of an inner surface of the peripheral wall of the barrel has a figure-8 shape in a plane perpendicular to the barrel axis, the figure-8 shape defining first and second cylindrical portions, a threaded lag screw for insertion within the first cylindrical portion of the passage, a compression nut for insertion within the first cylindrical portion of the passage and having a threaded internal surface for engagement with a threaded proximal end of the lag screw, a post for insertion within the second cylindrical portion of the passage through the fixation element, and a threaded fixation screw for insertion through a screw hole at an end of the plate. In accordance with other embodiments of the second aspect, the post may have a flange and the compression nut may have a groove configured for engagement with the flange of the post.

A third aspect of the present invention is a method of using a fracture fixation system, including drilling a superior bore through the femoral neck and into the femoral head, drilling an inferior bore through the femoral neck and into the femoral head to at least partially overlap the superior bore to create a bore hole having a figure-8 shape, mounting a fixation element to the femur, including placing an inner surface of a plate of the fixation element against an exterior surface of the femur, and inserting a peripheral wall of a barrel of the fixation element into the bore hole, the peripheral wall protruding from the inner surface of the plate and having a figure-8 shape in a plane perpendicular to a barrel axis along which the barrel extends, and inserting a monolithic peg into a passage defined through the plate and the barrel of the fixation element such that a distal end of the peg extends into communication with the femoral head, a body of the peg having an outer surface defining a figure-8 shape in a plane perpendicular to a peg axis along which the peg extends.

In accordance with other embodiments of the third aspect, the method may further include inserting a k-wire through a femoral neck and into a femoral head before the steps of drilling the first and second bores. The step of drilling the superior bore may include drilling the superior bore over the k-wire. The step of mounting may include guiding the passage of the fixation element over the k-wire. The step of inserting may include guiding a lumen of a superior cylindrical portion of the peg over the k-wire.

The step of drilling the superior bore may include drilling the superior bore with a first outer diameter, and the step of drilling the inferior bore may include drilling the inferior bore with a second outer diameter smaller than the first outer diameter. The method may further include inserting a threaded lag screw through a lumen of an inferior cylindrical portion of the peg and into the femoral head. The method may further include inserting a threaded fixation screw through a screw hole in the plate and into a diaphysis of the femur.

The figure-8 shape bore hole and the figure-8 shape of the peripheral wall of the fixation element may be substantially similar in size and shape. The step of inserting may include sliding a groove on an outer surface of the peg into engagement with a hook of a spring arm defined by a portion of the peripheral wall of the barrel, wherein the groove extends from a distal end of the peg only along a portion of a length of the peg and defines an end wall that limits distal movement of the peg when the hook contacts the end wall. The step of inserting may include inserting the peg until a hook of a spring arm defined by a portion of the peripheral wall of the barrel engages a groove in an outer surface of the peg, wherein the groove extends distally to an end wall that limits proximal movement of the peg when the hook of the spring arm contacts the end wall.

The step of inserting may include sliding a first groove in an outer surface of the peg into engagement with a hook of a first spring arm defined by a portion of the peripheral wall of the barrel, wherein the first groove extends from a distal end of the peg only along a portion of a length of the peg and defines a first end wall that limits distal movement of the peg when the hook of the first spring arm contacts the first end wall, and inserting the peg until a hook of a second spring arm defined by a portion of the peripheral wall of the barrel engages a second groove in an outer surface of the peg, wherein the second groove extends distally to a second end wall that limits proximal movement of the peg when the hook of the second spring arm contacts the second end wall. The first and second grooves may at least partially overlap along the peg axis. A floor of the second groove may be tapered to be shallower at the second end wall to bias the peg proximally along the barrel axis.

A fourth aspect of the present invention is a method of using a fracture fixation system, including drilling a superior bore through the femoral neck and into the femoral head, drilling an inferior bore through the femoral neck and into the femoral head to at least partially overlap the superior bore to create a bore hole having a figure-8 shape, assembling a monolithic peg into a passage defined through a plate and a barrel of a fixation element, a peripheral wall of the barrel protruding from an inner surface of the plate and having a figure-8 shape in a plane perpendicular to a barrel axis along which the barrel extends, a body of the peg having an outer surface defining a figure-8 shape in a plane perpendicular to a peg axis along which the peg extends, and mounting the fixation element together with the monolithic peg to the femur, including placing the inner surface of the plate against an exterior surface of the femur, and inserting the peripheral wall of the barrel together with at least a portion of the monolithic peg into the bore hole such that a distal end of the peg extends into communication with the femoral head.

Provided herein are implants designed to fix fractures in bone, and in particular in the femur. A fixation element includes an exterior component of a plate, and an interior component of a barrel, the latter of which is to be disposed within a portion of the bone. The barrel is non-circular in cross-section so that it can inhibit rotation and maintain a stronger fixed orientation of the fractured bone components during healing. A similarly configured, non-circular peg can be disposed within the barrel and extended further into the bone. Either through or in conjunction with the peg, a lag screw can be incorporated to create fixation within the deeper portion of the fractured bone to structurally fix the portion to the implanted system. Various components that facilitate the interconnection between the barrel and the peg and the lag screw permit fixation while applying compressive forces and also permitting additional compressive movement of the fractured bone components during healing. In some variations, a non-circular peg is inserted deeper into the bone. In other variations, a lag screw and a separate post are inserted deeper into the bone adjacent one another.

BRIEF DESCRIPTION OF THE DRAWINGS

The drawings described herein are for illustrative purposes only of the selected embodiments and are not all possible implementations and thus are not intended to limit the scope of the present disclosure.

DETAILED DESCRIPTION

Referring to FIGS. 1-9, a first embodiment of a fracture fixation system 1 includes a fixation element 8 and a peg 10. The system 1 utilizes a single load-bearing peg 10 installed into the neck-head fragment of the femur, placed together with a lateral flange as described below. Distal fixation can be achieved by the insertion of variable locking screws or any other type of fixation screw.

Figure 1:
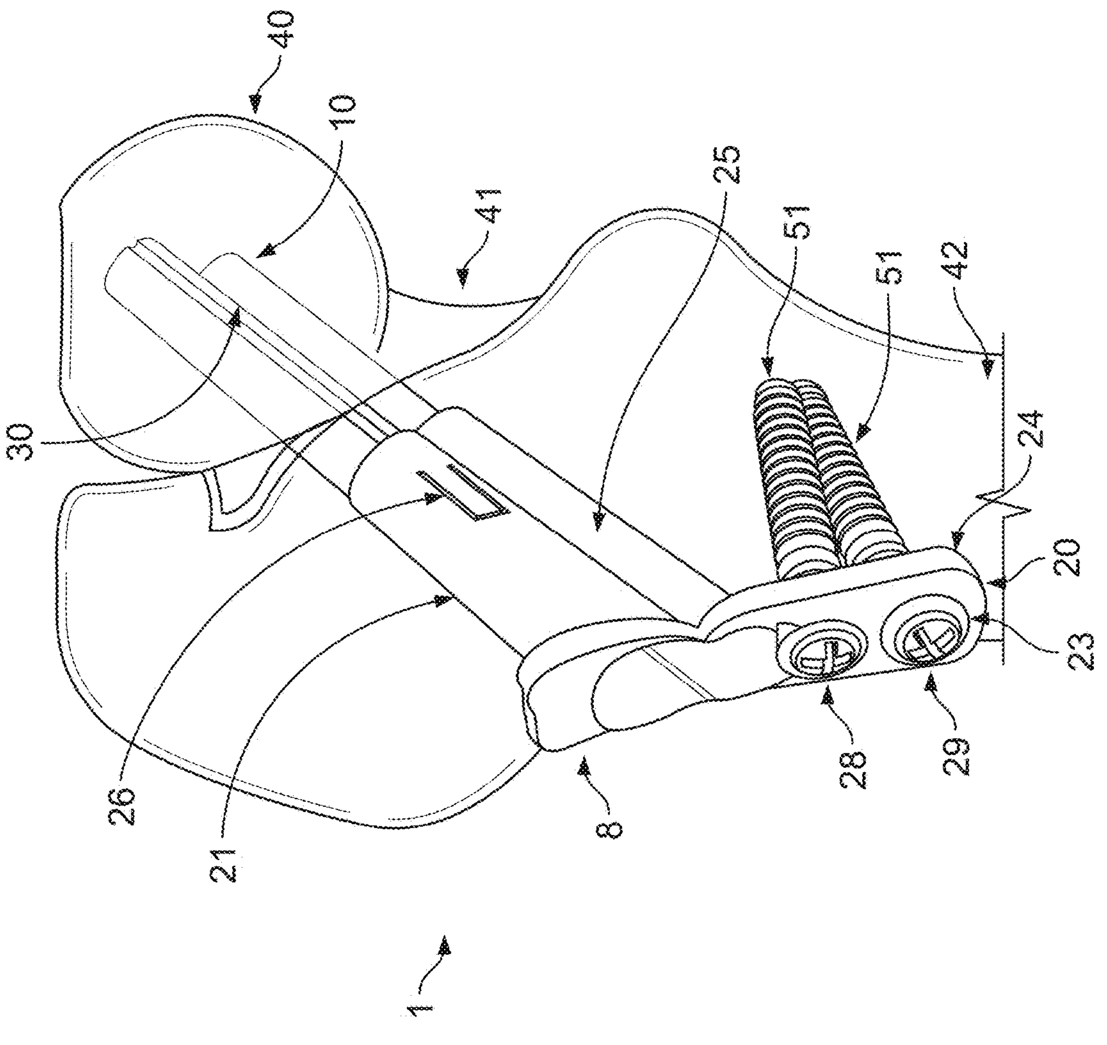
FIG. 1 is a perspective view of an embodiment of a fracture fixation system.
Figure 3:
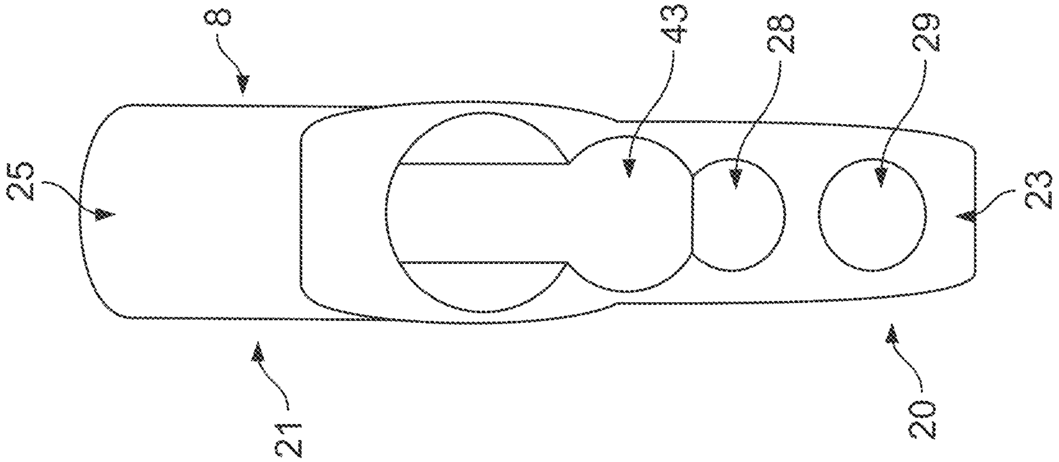
FIGS. 2 and 3 are perspective and side views, respectively, of a fixation element of the fracture fixation system shown in FIG. 1.
Figure 2:
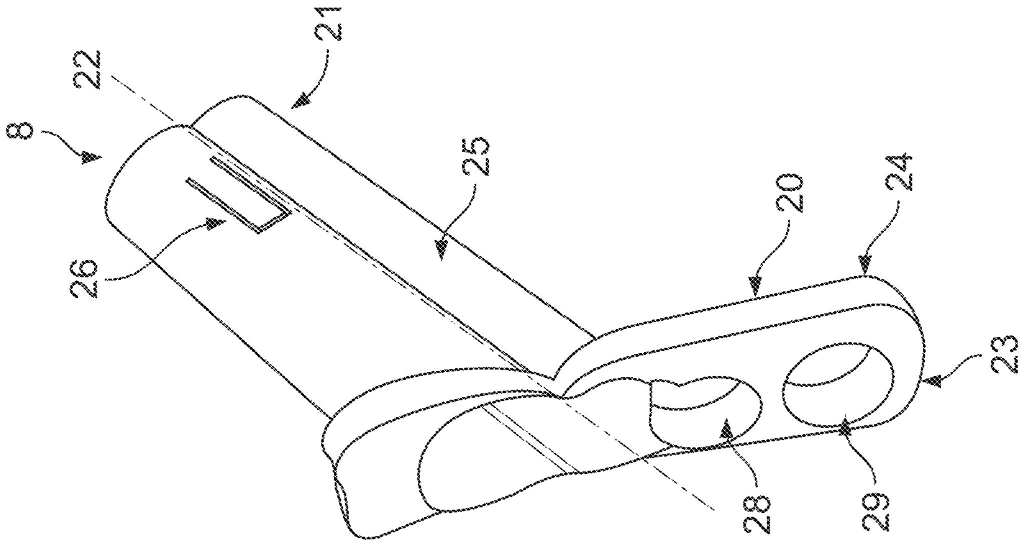

As shown in FIGS. 1-3, the fixation element 8 is comprised of a plate 20 and a barrel 21. Plate 20 can be monolithically attached to barrel 21 such that the two are integrally formed as one single piece. In other embodiments, plate 20 and barrel 21 can be distinct elements that are joined or connected together in use. The plate 20 has an outer surface 23 spaced from an inner surface 24, which can be placed against an exterior surface of a bone 42 as shown in FIG. 1. The barrel 21 extends along a barrel axis 22 and has a peripheral wall 25 that protrudes or extends from the inner surface 24 of the plate 20. The barrel 21 can be manufactured based on patient-specific data to a particular size, shape, and profile, which aids in effectively controlling varus forces. The fixation element 8 is designed for use with a proximal femur, such that in use the plate 20 is disposed at an outer lateral surface of the femur, and the barrel 21 extends from that surface towards and into the femoral neck. The fixation element 8 defines a passage that extends through the plate 20 from the outer surface 23 through the barrel 21 within peripheral wall 25, which extends along the barrel axis 22.

As shown in FIGS. 1-3, the peripheral wall 25 of the barrel 21 is located nearer to a first or superior end of the plate 20 than to an opposed second or inferior end of the plate 20. This allows the second inferior end of the plate 20 to extend down the shaft of the femur for additional fixation. The second end of the plate defines two screw holes 28 and 29, and two threaded fixation screws 51 can be inserted through the two screw holes 28 and 29, respectively, and into the femoral bone to anchor fixation element 8 securely to the bone. A figure-8 shape is defined by the inner surface 24 of the peripheral wall 25 and comprised of overlapped cylindrical surfaces. A larger of the cylindrical surfaces is nearer to the first or superior end of the plate 20 than to the second inferior end of the plate 20.

Figure 12:
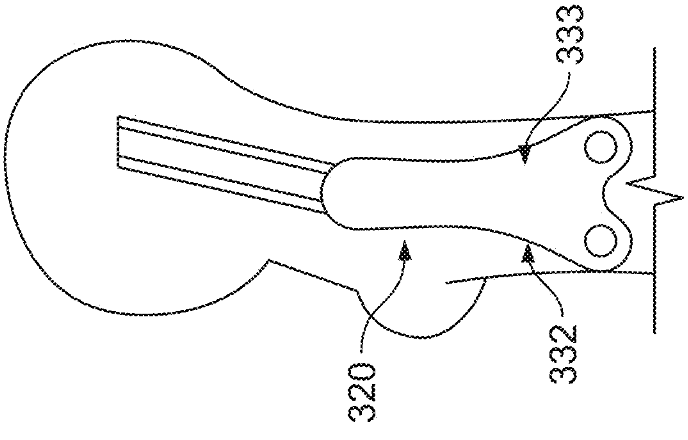
FIG. 12 is a side view of a plate of a fracture fixation system of an alternative embodiment.

In other embodiments such as the one shown in FIG. 12, the second inferior end of plate 320 can have a perimeter with a dovetail shape, which is designed to limit the distal length and to potentially ensure distal screw placement of the tip of a retrograde nail. In such an embodiment, the plate 320 includes a left side 332 and a right side 333 each extending from the first superior end to the second inferior end, and the second end includes one hole on the left side and one hole on the right side. The placement of these holes is designed to avoid a central canal of the femur in case a retrograde nail is disposed therein.

Referring to FIGS. 1 and 4-9, the peg 10 of the fracture fixation system 8 is configured for insertion into the passage of the barrel 21 and extends along a peg axis 11. The body of the peg 10 has an outer surface 12 defining a figure-8 shape in a plane perpendicular to the peg axis 11. In a similar manner, an inner surface 43 of the peripheral wall 25 of the barrel 21 has a figure-8 shape in the plane perpendicular to the barrel axis 22. The figure-8 shape of the outer surface 12 of the peg 10 corresponds to and matches the figure-8 shape of the inner surface 43 of the peripheral wall 25 of the barrel 21, so that a non-rotational interlocking fit can be achieved when the peg 10 is disposed within the barrel 21. That is, the figure-8 shape of the outer surface 12 of the peg 10 is substantially similar in size and shape or congruent to the figure-8 shape of the peripheral wall 25 of the barrel 21. This provides an angularly stable and dynamic construct.

Figure 4:
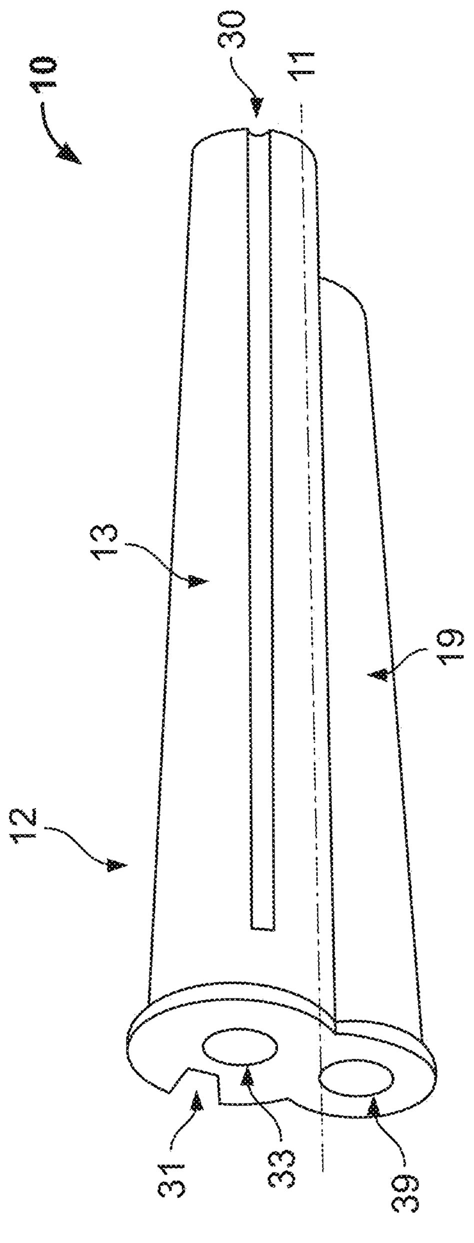
FIGS. 4 and 5 are perspective views of a peg of the fracture fixation system shown in FIG. 1.
Figure 5:
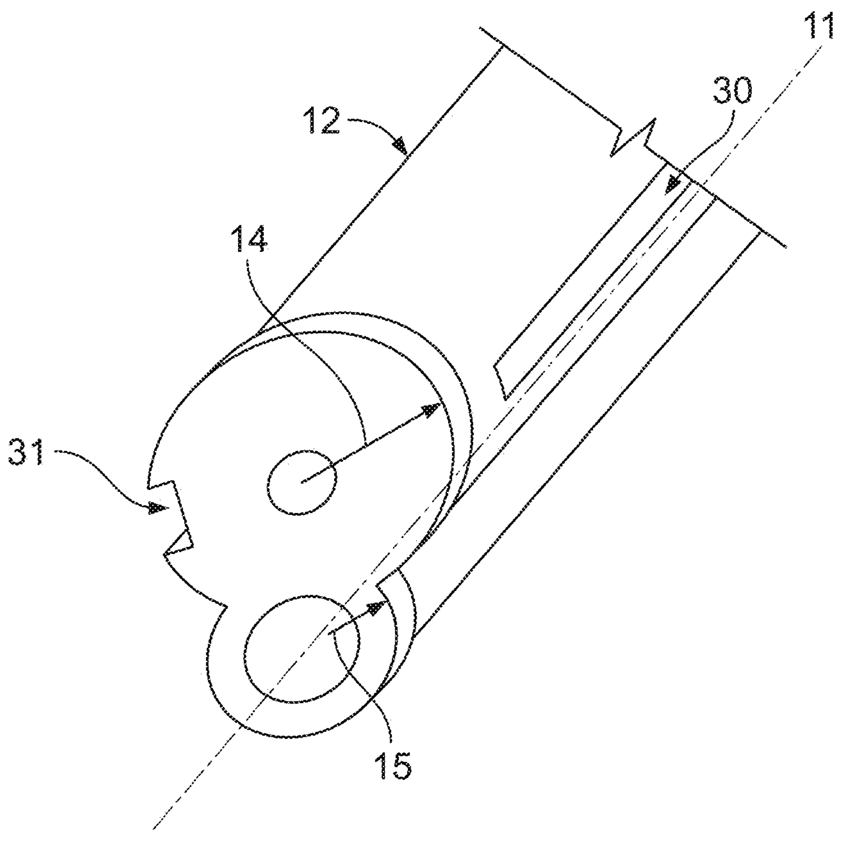
Figure 6:
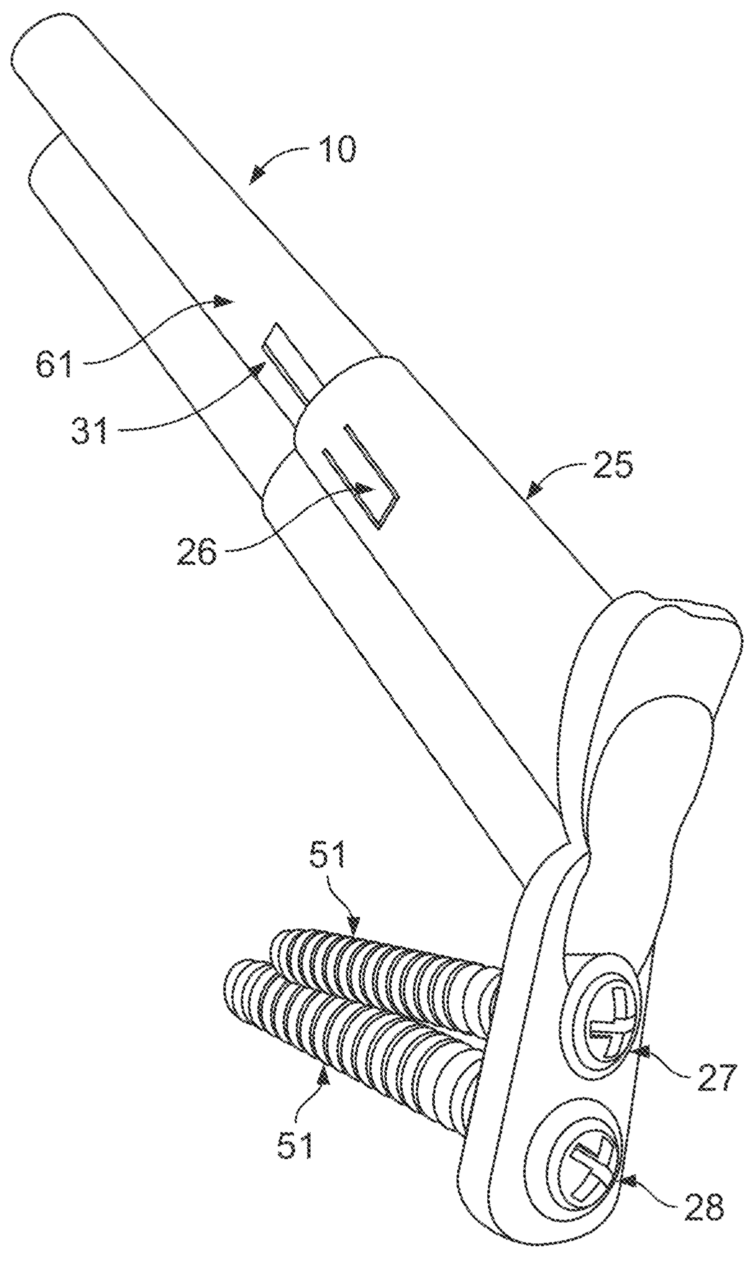
FIG. 6 is an assembled perspective view of the fracture fixation system shown in FIG. 1 with two threaded fixation screws.
Figure 7:
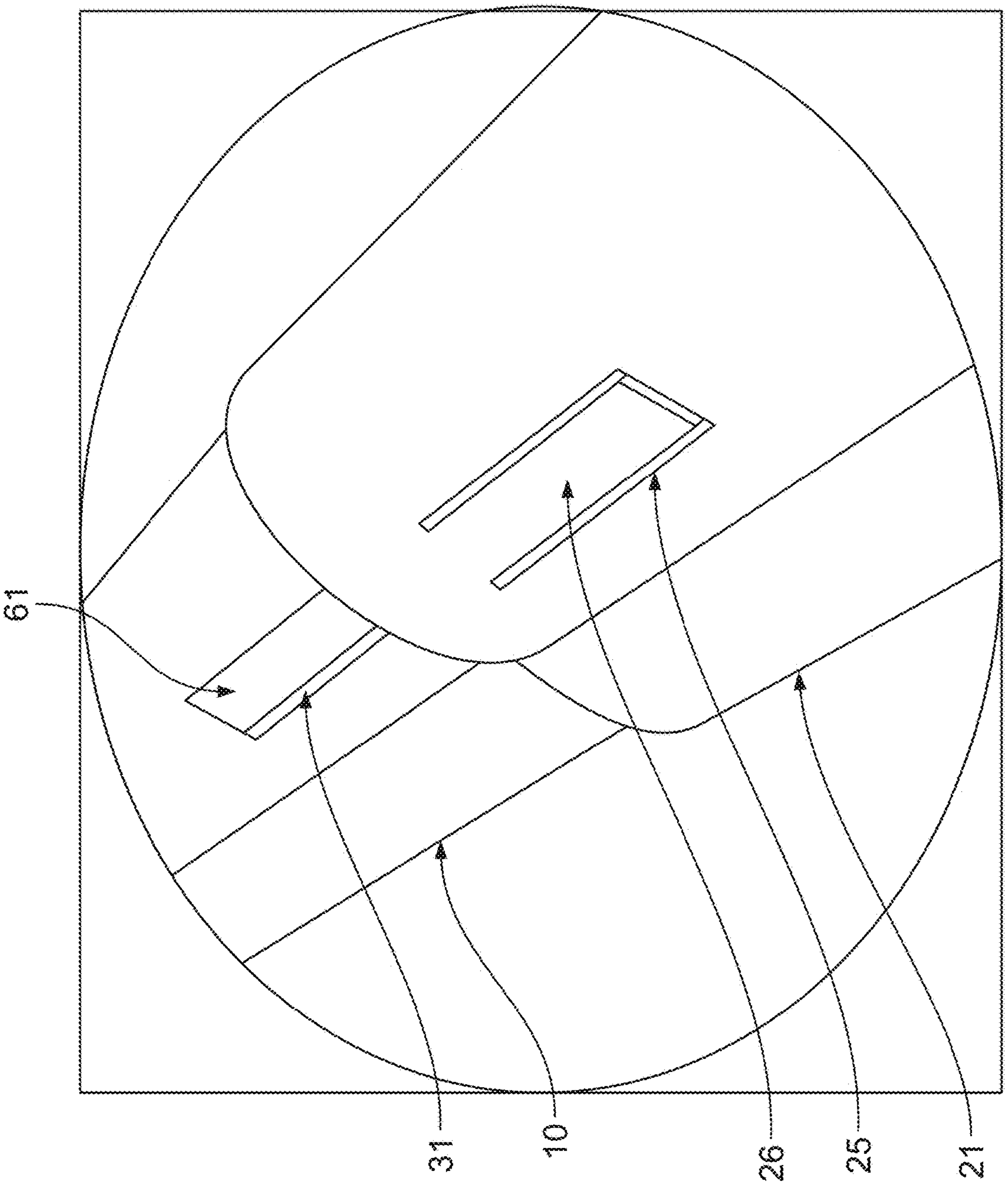
FIG. 7 is an enlarged perspective view of a portion of an outer surface of the peg and the fixation element of the fracture fixation system shown in FIG. 1.
Figure 8:
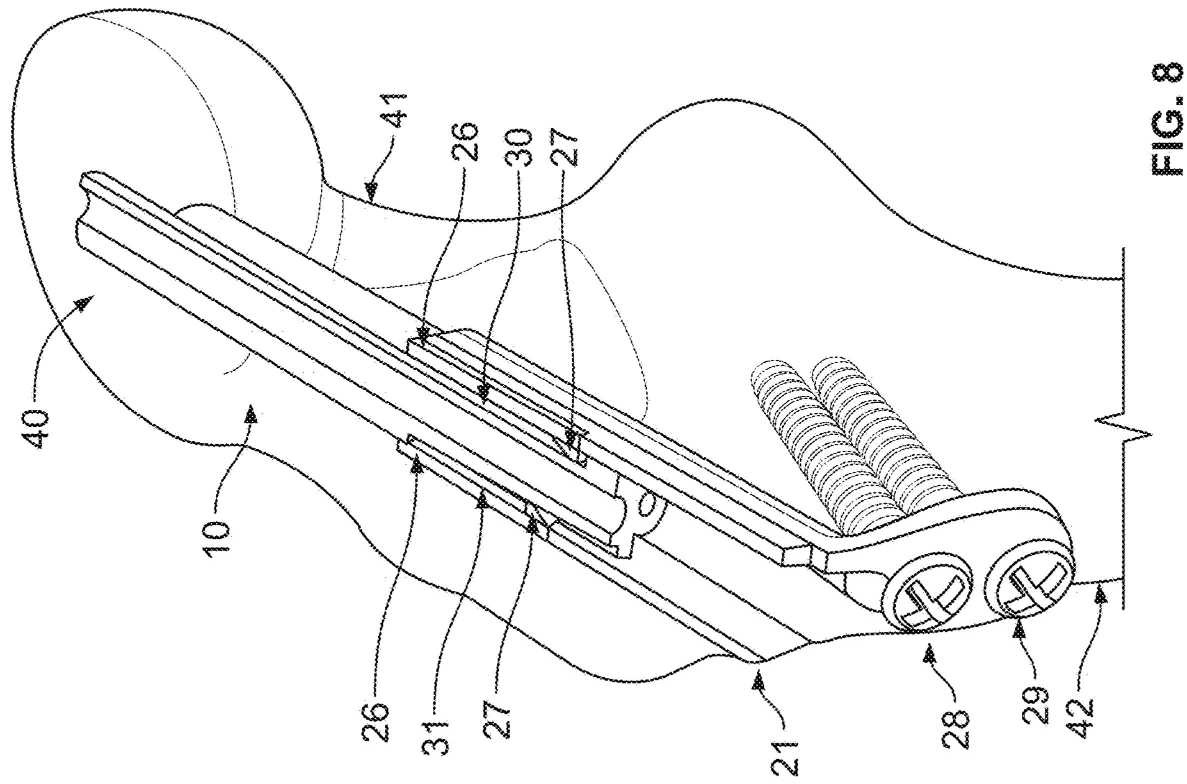
FIGS. 8 and 9 are partially cut-away views of the fracture fixation system as shown in FIG. 1.

The peg 10 is comprised of overlapped cylindrical portions that define the figure-8 shape of its outer surface 12, as seen in FIG. 4. This includes a larger cylindrical portion 13 defined by a larger radius 14 and a smaller cylindrical portion 19 defined by a smaller radius 15, as shown in FIG. 5. In other embodiments, radii 14 and 15 can be identical. Alternatively, the outer surface 12 of the peg 10 may be formed by any two non-rotational symmetrical shapes that are overlapped to form a single body. The peg 10 may be monolithic or comprised of multiple components. That is, each cylindrical portion 13, 19 may be a distinct element and joined together for use with barrel 21. With the larger cylindrical portion 13 configured to be superior in an implanted configuration, an inverted figure-8 shape of the peg 10 is achieved, which allows appropriate cut-out resistance while maintaining sufficient post-operative rotational control.

While the described figure-8 shapes are particular to the illustrated embodiment, any non-circular shapes can be used, such as oval, triangular, etc. The non-circular perimeter stabilizes the fixation system 8 within the bone to resist rotation of the bone fragments during healing. Additionally, the positioned larger and smaller cylindrical portions of the figure-8 shape are positioned for use with a lag screw in the inferior portion. However, the cylindrical portions can be of the same size or could alternatively be inverted. In other embodiments, a cylindrical shape could be used with two offset holes so that fixation elements can be inserted to create a non-rotational fixation.

The larger and smaller cylindrical portions 13, 19 of the peg 10 each define a lumen 33, 39, respectively. In one embodiment, the lumen 39 of the smaller cylindrical portion 19 has an internal diameter that is larger than an internal diameter of the lumen 33 of the larger cylindrical portion 13. In an alternative embodiment, the diameters of the lumens 33, 39 may be identical. In use, the larger cylindrical portion 13 provides lumen 33 as a cannulation to allow insertion over a guide wire, for example. The lumen 39 of the smaller cylindrical portion 19 offers the option to insert a dedicated instrument such as a screw to actively apply compression, or apposition, intraoperatively.

The larger and smaller cylindrical portions 13, 19 also have different maximum lengths along the peg axis 11, wherein the smaller cylindrical portion 19 is shorter than the larger cylindrical portion 13 of the peg 10. These lengths are measured from the terminal end of the respective cylindrical portion. Both lengths are still longer than a length of the barrel 21 as measured from plate 20 to an opposite terminal end of barrel 21. The shorter length of smaller cylindrical portion 19 permits insertion of a lag screw that extends past its distal end, as described below. In other embodiments, perhaps in which a lag screw may not be intended for use, the lengths of the cylindrical portions 13 and 19 can be the same or inverted.

Figure 9:
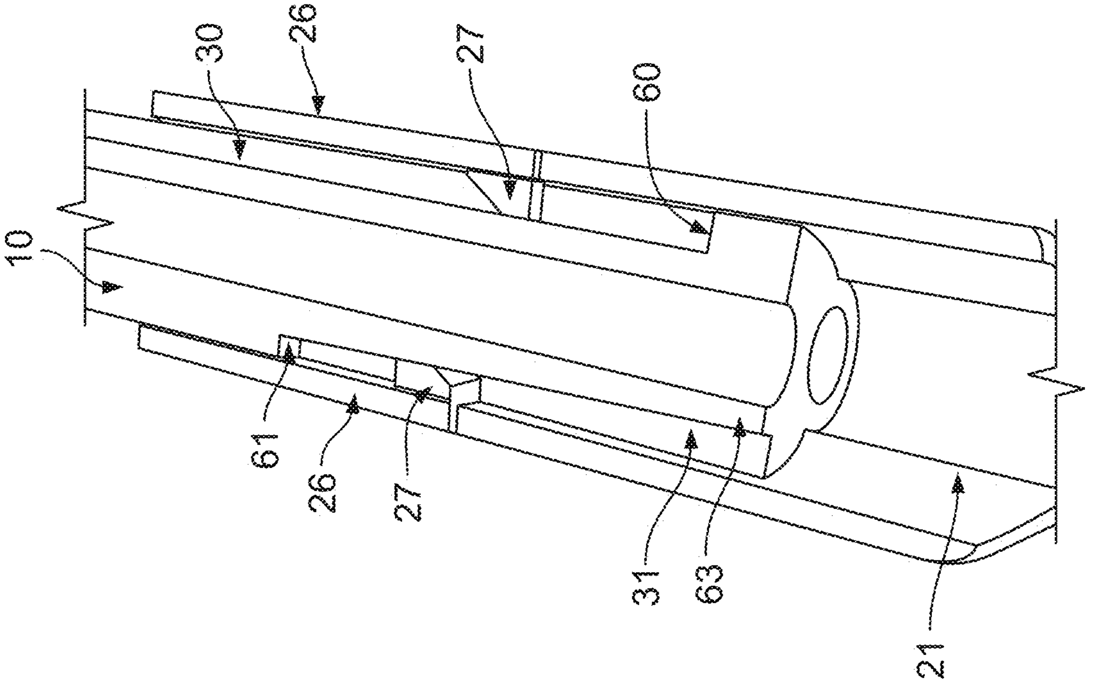

Fracture fixation system 1 includes a mechanism to limit travel of peg 10 within barrel 21 of fixation element 20. Referring to FIGS. 6-9, a portion of the peripheral wall 25 of the barrel 21 defines two spring arms 26 each with a hook 27 extending inward toward a center of barrel 21. In this way, spring arms 26 are connected only at one end to the remainder of peripheral wall 25 so that they act as cantilever beams. The hooks 27 are at the ends of spring arms 26 opposite to the connected ends so that the hooks can flex inward and outward with respect to the inside of peripheral wall 25. Hooks 27 are configured for engagement with respective grooves 30 and 31 in the outer surface 12 of the peg 10. Each groove 30 and 31 of extends only along a portion of a length of the peg 10. In this way, groove 30 defines an end wall 60 at one end nearer plate 20 and extends to an open end at the opposing end of peg 10 further from plate 20 when peg 10 and fixation element 8 are assembled. Oppositely, groove 31 defines an end wall 61 that is further from plate 20 and extends to an open end at the opposing end of peg 10 nearer plate 20. Hooks 27 are generally located the same or a similar location along barrel axis 22. As can be seen in FIG. 9, the end walls 60 and 61 are spaced apart or misaligned along the peg axis 11 so that peg 10 can move along peg axis 11 and barrel axis 22 when assembled with fixation element 8 between a distance that separates end walls 60 and 61. That is, grooves 30 and 31 at least partially overlap along the peg axis 11. Further movement in either direction along the axes is opposed by the abutment of a hook 27 with an end wall 60, 61. In this way, each hook 27 limits movement of the peg 10 within the passage when the hook 27 contacts the end wall 60 and 61. The hook-spring design feature is useful in controlling uncontrolled medialization of the peg and excessive shortening of the femoral neck.

Groove 31 has a floor 63 that is tapered such that it is shallower at the end wall 61 than it is at the end of the peg 10 nearer plate 20, as shown in FIG. 9. Groove 30 has a floor 62 that is at a substantially constant depth along the entire length of groove 30. This tends to permit lateral movement of peg 10 within barrel 21 to promote stabilization and healing of a femoral neck fracture. In other words, appropriate shaping of the spring and groove may be suited to integrate a force dependent shortening of the femoral neck 41.

Figure 10:
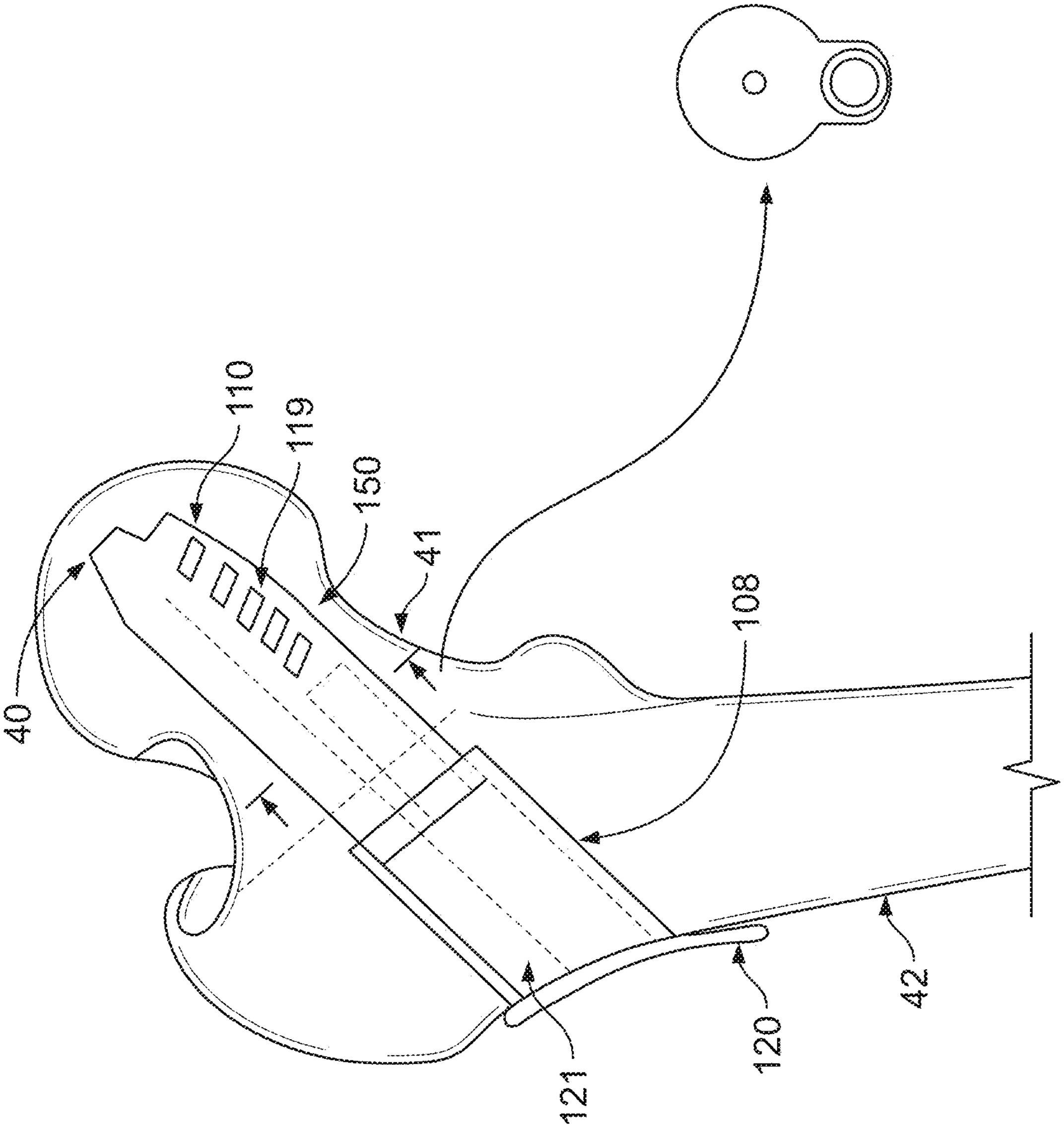
FIGS. 10 and 11 are depictions of alternative embodiments of a fracture fixation system implanted in a femur with a threaded lag screw.
Figure 11:
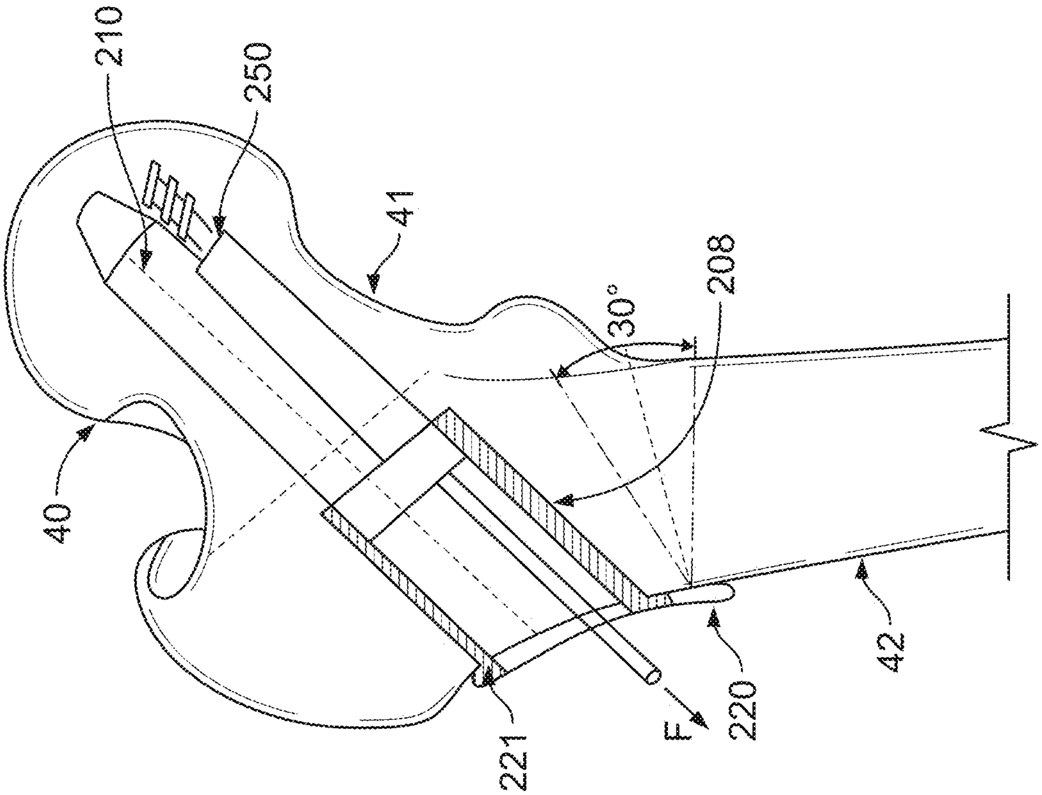

To allow compression or apposition, an additional threaded instrument can be utilized and inserted into the inferior smaller cylindrical portion 119 of peg 110. For example, as shown in FIG. 10, a threaded lag screw 150 can be provided that includes anterior/posterior engaging thread flanks. In this case, the smaller cylindrical portion 119 of the peg 110 can be flat on the anterior/posterior sides as shown and can be used with a fixation element 108 having a plate 120 and a barrel 121. In FIG. 11, a different peg 210 is provided for use with a threaded lag screw 250 having medial penetrating threads in connection with a fixation element 208 having a plate 220 and a barrel 221. The respective plates 120 and 220 of fixation elements 108 and 208 can also be provided with two screw holes, and two threaded fixation screws can be disposed through the two screw holes, respectively, as described above.

The modular nature of the elements of system 1 permit using a fixation element 8 and a peg 10 with one or more lag screws and one or more fixation screws as desired or as permitted based on the anatomy and bone fidelity of a particular patient. For example, a kit of a fracture fixation element can include at least one threaded lag screw and at least one threaded fixation screw.

A method of using the fracture fixation system 1 described above includes a preliminary step of inserting a k-wire through the femoral neck 41 and into a femoral head 40. While this step is not required, it is useful to align the following drilling and insertion steps. Next, superior and inferior bore holes are drilled through the femoral neck 41 and into the femoral head 40, such that the bore holes at least partially overlap to create a bore hole having a figure-8 shape. This shape can match any desired silhouette or outline of a barrel as described above, such that the figure-8 shape of the bore hole and the figure-8 shape of the peripheral wall 25 of the barrel 21 to be used are substantially similar in size and shape. For example, the inferior bore hole can be of a smaller diameter than the superior bore hole. Assuming a k-wire is used, at least the superior bore is drilled over the k-wire using a cannulated drill bit.

The fixation element 8 is mounted to the femur 42, including placing the inner surface 24 of the plate 20 against an exterior surface of the femur 42 and inserting the peripheral wall 25 of the barrel 21 into the bore hole. The peg 10 is inserted into a passage defined through the plate 20 and the barrel 21 of the fixation element 8 such that a distal end of the peg 10 extends into communication with the femoral head 40. Again, assuming the k-wire is used, these steps can include guiding the passage of the fixation element 8 over the k-wire and guiding the lumen 33 of the larger cylindrical portion 13 over the k-wire. The peg 10 can be preloaded into the fixation element 8 without the need for any tooling, so that the steps of inserting the fixation element 8 and the peg 10 are carried out together, for example with a targeting device or other insertion instrument.

During the insertion of the peg 10 into the barrel 21, the groove 30 of the peg 10 engages and slides along the hook 27 of the spring arm 26 such that the peg 10 can be inserted up to a point at which the hook contacts the end wall 60 to limit further distal movement of the peg 10. Insertion all the way to end wall 60 is not necessarily required as this is an outer limit of movement of the peg 10 within the barrel 21, and in fact a position before hook 27 abuts end wall 60 is preferable. Using this design is beneficial to stop or otherwise limit the distance that the femoral head 40 is free to move in the lateral direction towards the trochanteric region of the femur. Limiting the movement in this manner helps to prohibit excessive compression of the weak bone adjacent to the fracture cite.

During this insertion, the other hook 27 of the other spring arm 26 flexes outward until it drops over the end wall 61 and into engagement with the groove 31 of the peg 10. Once the hook 27 moves into the groove 31, this prevents further proximal movement of the peg. The overlap of the grooves 30 and 31 along the peg axis 11 gives the peg 10 a range of adjustment or motion within the barrel 21 as healing of the femur 42 occurs. More specifically, the tapered floor 63 the groove 31 tends to bias the peg 10 proximally along the barrel axis 22. This design of grooves 30 and 31 creates a spring-type design to control both an uncontrolled medialization of the peg 10 and an excessive shortening of the femoral neck. Appropriate shaping of the spring and tapered floor 63 can be provided to integrate a force-dependent shorting of the neck.

A threaded lag screw 50*a* or 50*b* can be inserted through the lumen 39 of the smaller cylindrical portion 19 of the peg 10 and into the femoral head 41. Alternatively, or additionally, one or more threaded fixation screws 51 are inserted through screw holes 28 and 29 in the plate 20 and into a diaphysis of the femur 42.

In an alternative method to that described above, either before or after the superior and inferior bore holes are drilled, the peg 10 can be assembled with the fixation element 8 prior to insertion of either component. That is, the peg 10 can be inserted into the passage defined through the plate 20 and the barrel 21 of the fixation element 8, i.e. while outside of the bone. Then, the peg 10 and the fixation element 8 can together be mounted to the bone by inserting the barrel 21 and at least a portion of the peg 10 into the bore hole to the position described above.

Figure 13:
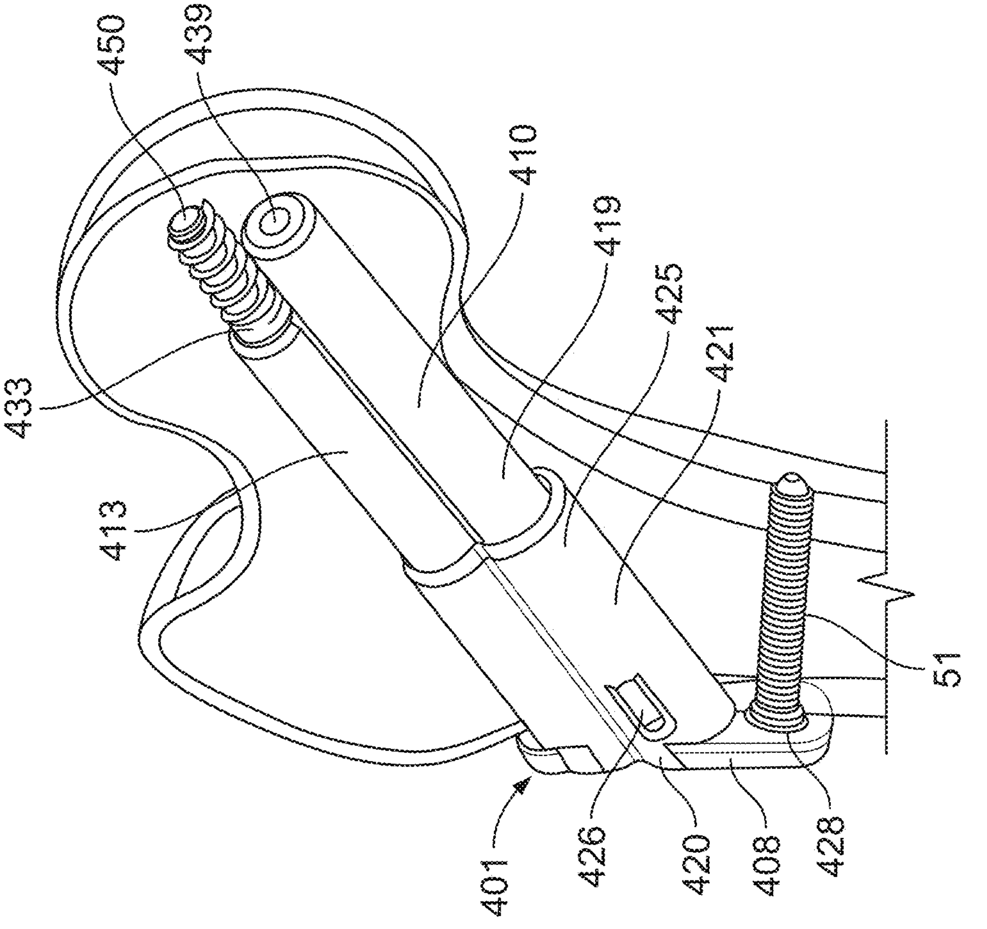
FIG. 13 is a perspective view of another embodiment of a fracture fixation system.

Another embodiment of a fracture fixation system 401 is shown in FIG. 13. System 401 includes a fixation element 408, a peg 410, a lag screw 450. The distal end of plate 420 includes one screw hole 428 through which threaded fixation screw 51 can be inserted into the adjacent bone. System 401 is relatively similar to the aforementioned systems with the different features and operations described below. Similar elements are numbered similarly to systems 100-300.

The peg 410 is comprised of overlapped cylindrical portions of substantially equal radii, with superior cylindrical portion 413 being shorter than inferior cylindrical portion 419. The lumen 433 of superior cylindrical portion 413 is larger than lumen 439 of inferior cylindrical portion 419, since lumen 433 is designed to accommodate a threaded lag screw 450 to enhance fixation within the distal portion of femoral head 40. Lag screw 450 is sized such that it can be inserted through superior cylindrical portion 413 from a proximal end thereof.

Barrel 421 has a spring arm 426 in the inferior portion of peripheral wall 425, with a hook on an internal surface thereof. Spring arm 426, which can be provided in multiple, cooperate with a positioning screw and a collar to create compression within the bone, as described more thoroughly in connection with system 501 described below.

Figure 15:
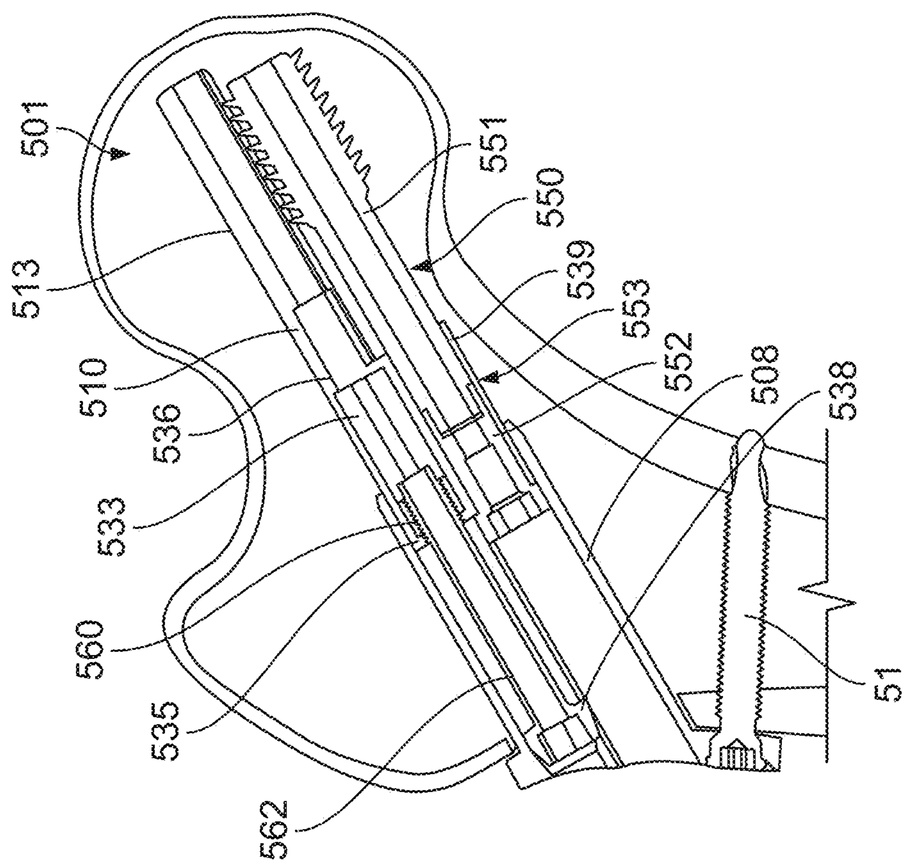
FIGS. 14 and 15 are perspective view and sectional views of another embodiment of a fracture fixation system.
Figure 14:
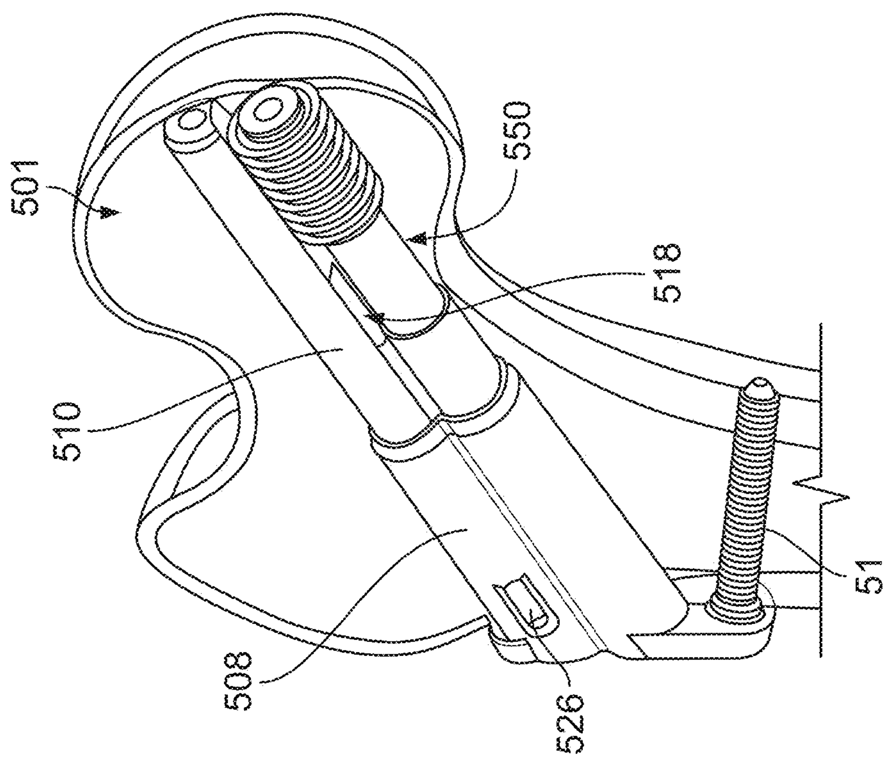

Shown in FIGS. 14 and 15 is another embodiment of a fracture fixation system 501 having a fixation element 508, a peg 510, a positioning screw 562, a fixation screw 51, and a lag screw 550. System 501 is relatively similar to the aforementioned systems with the different features and operations described below. Similar elements are numbered similarly to systems 100-400.

Lag screw 550 is a two-part design, having a threaded distal end 551 and a proximal end 552 with a tool engaging portion. Ends 551 and 552 connect at a junction 553 at which distal end 551 has an extension that threads or otherwise connects into a depression in the end of proximal end 552. The threaded connection between ends 551, 552 is of the same direction as the threads at the bone engaging portion of distal end 551 to ensure that rotation of proximal end 552 is properly transferred into rotation of screw 550 as a whole into bone.

Both the threaded component of distal end 551 and the head on proximal end 552 are of a larger diameter than the internal lumen 539 of peg 510, so that the relatively larger head of proximal end 552 provides a stop against excessive distal positioning of lag screw 550 when the head contacts a proximal end of peg 510 at lumen 539. The two-part design of lag screw 550 requires preinstallation with peg 510 and fixation element 508 before any of such components are installed. That is, lag screw 550 is assembled into lumen 539, and peg 510 is installed within fixation element 508 prior to insertion within the bone. These installation steps can be carried out in either order.

Lumen 533 of superior cylindrical portion 513 of peg 510 defines a cavity in which a threaded collar 560 is disposed for engagement with positioning screw 562. Threaded collar 560 can be 3D printed with peg 510 so that it is disposed within lumen 533, or else can be manufactured separately and loaded through a window 518 in superior cylindrical portions 513. Collar 560 has a noncircular outer surface that engages with a noncircular inner surface of lumen 533 so that collar 560 is configured to move axially within but not to rotate within lumen 533. The cavity 534 of lumen 533 in which collar 560 is disposed has proximal and distal ends 535, 536 to limit travel of collar 560 within lumen 533.

Positioning screw 562 is threaded into lumen 533 and into engagement with the threaded inner surface of collar 560. A head 537 of positioning screw 562 has a noncircular recess for engagement with a tool and is larger in diameter than a shaft of screw 562 such that head 537 defines a shoulder 538 that is configured to engage spring arm 526. More specifically, spring arm 526 includes a hook like hook 27 described above. The hook on the inner surface of spring arm 526 is configured to engage shoulder 538 of head 537 to prevent distal movement of positioning screw 562 toward the femoral head. While one spring arm 526 is shown in FIG. 14, two similar spring arms are disposed on opposite sides of fixation element 508 to engage with shoulder 538. More or fewer spring arms with hooks can also be provided.

In use, after preassembly of system 501, which can include assembly of positioning screw 562 into collar 560, system 501 can be inserted into a predrilled bore within the bone as described above. Lag screw 550 can then be rotated to advance lag screw and peg 510 into a desired depth and position within the femoral head. As shown in FIG. 14, a channel or recess along the distal portion of peg 510 adjacent the threaded distal end 551 of lag screw 550 permits close positioning of the distal ends of peg 510 and lag screw 550 without contact therebetween. During this insertion step, positioning screw 562 can be positioned so that it is extended proximally from peg 510 so that it does not contact spring arms 526 to hinder the proper depth and positioning of lag screw 550 and peg 510. In other embodiments, positioning screw 562 can be omitted from the initial preassembly and inserted after lag screw 550 and peg 510 are disposed in their intended locations within the bone.

Once positioning screw 562 is engaged with collar 560, positioning screw 562 can be rotated by a driver to cause compression within the bone by pulling peg 510 and lag screw 550 proximally. This occurs as positioning screw 562 is rotated within fixation element 508, where distal movement of positioning screw 562 is prevented once shoulder 538 contacts the hook of spring arm(s) 526. Further rotation of positioning screw 562 causes collar 560 to move proximally toward positioning screw 562 within lumen 533 until collar 560 contacts proximal end 535 of lumen 533. During this movement, collar 560 is not permitted to rotate due to its noncircular connection to lumen 533. Thus, continued rotation of positioning screw 562 after collar 560 is in contact with proximal end 535 of lumen 533 pulls collar 560, peg 510, and lag screw 550 proximally with respect to positioning screw 562 and fixation element 508, creating a compressive force on the bone. Upon further healing of the bone after system 501 is implanted, additional sliding movement of collar 560, peg 510, and lag screw 550 are permitted due to the non-threaded connection of collar 560 with lumen 533.

Figure 17:
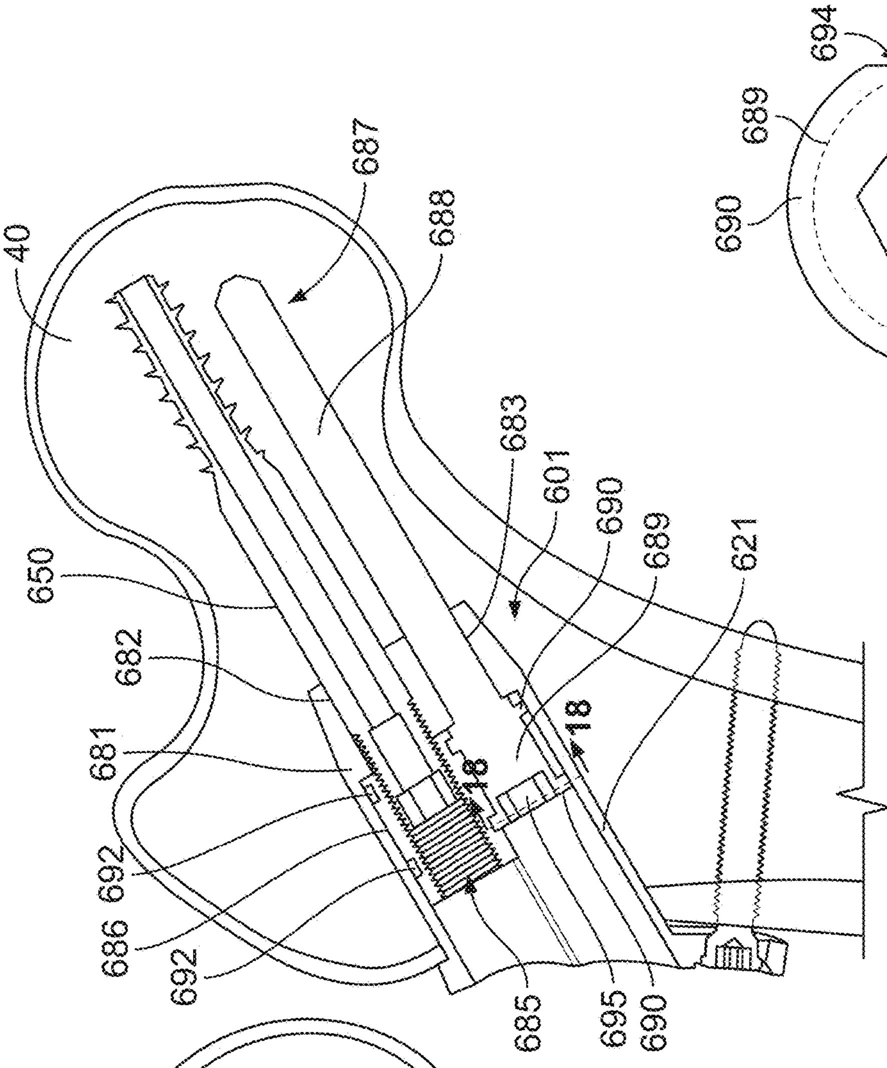
FIGS. 16 and 17 are perspective view and sectional views of another embodiment of a fracture fixation system.
Figure 18:
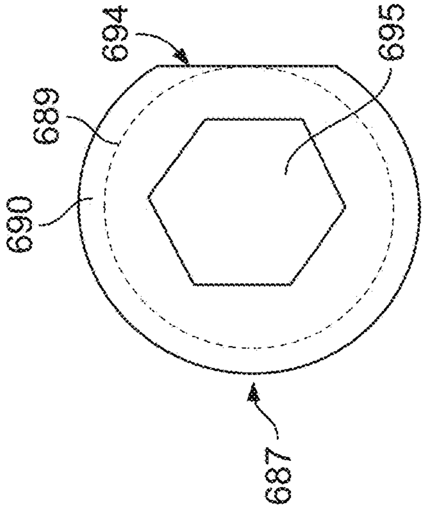
FIG. 18 is a top view of a post of the fracture fixation system of FIG. 17 taken along line 18-18.
Figure 16:
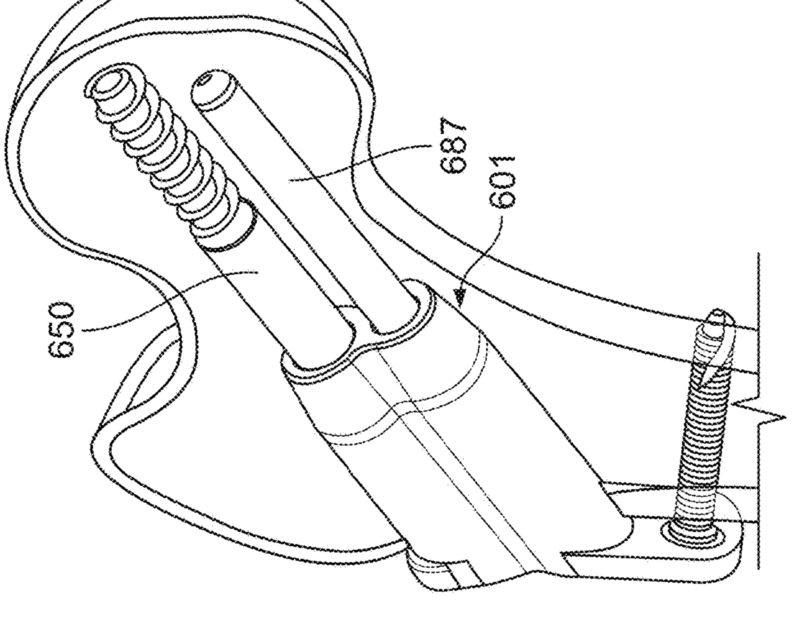

A further embodiment is shown in FIGS. 16-18 of fracture fixation system 601. System 601 is similar to the aforementioned embodiments in that barrel 621 defines a figure-8 shape along its internal peripheral wall, with this figure-8 shaped passage terminating at a junction 681 within the barrel 621. Distal of this junction 681, a superior passage 682 and an inferior passage 683 extend separately and distinctly, without overlap to the terminal distal end of barrel 621.

Within the superior bore of barrel 621, which is made up of the superior portion of the figure-8 shaped passage along with superior passage 682, a lag screw 650 is disposed to extend into femoral head 40. The distal end of lag screw 650 is threaded for securing within the bone. The proximal end of lag screw 650 is also threaded for engagement with a compression nut 685 that is disposed within superior portion of barrel 621. Lag screw 650 is cannulated for a K-wire to be inserted therethrough during insertion of the system 601. A proximal end of the lag screw 650 also includes a non-circular recess for engagement with a tool so that lag screw 650 can be rotated during insertion.

Nut 685 has a generally cylindrical outer surface 686 so that it can rotate within the superior portion of barrel 621, and can move axially within barrel 621 up to junction 681. Because of this, lag screw 650 can be rotated along its axis to secure it within the bone without its rotational motion being dependent on its axial position within barrel 621. That is, lag screw 650 is configured to move axially within barrel 621 independently of its rotation with respect to barrel 621. Because lag screw 650 is threadedly engaged with nut 685, when lag screw 650 is rotated and nut 685 is free to rotate with it, there is no relative rotation between lag screw 650 and nut 685, in which case nut 685 can provide a depth stop to the extent of insertion into the bone by lag screw 650 when nut 685 bottoms out at junction 681. In other embodiments, nut 685 is located proximally such that lag screw 650 can be inserted to a desired depth without nut 685 contacting junction 681. Moreover, while holding lag screw 650 rotationally fixed with a tool, nut 686 can be rotated around lag screw 650 either to set a different location of this distal stopping point, or, when nut 685 is in contact with junction 681, to pull lag screw 650 proximally within barrel 621 to create compression across the fracture site within the bone due to the engagement of the distal threads of lag screw 650 within the bone. To permit rotation of nut 685, its proximal end has a hexagonal interface disposed on the inner surface, interrupting any threads, to facilitate connection with a driver. Use of a driver to hold lag screw 650 from rotating, while use of another driver to rotate nut 685 can cause nut 685 to move along the axis of lag screw 650, particularly to provide compression. These two drivers can be combined into one double-action driver.

A post 687 is provided within inferior portion of barrel 621 and extends past junction 681 and into the femoral head 40. Post 687 has a shaft 688 of a diameter that fits within the inferior passage 683, and a proximal end 689 of a relatively larger diameter that prohibits further distal movement of post 687 from the position shown in FIG. 17, i.e. when proximal end 689 is in contact with junction 682. This larger proximal end 689 of post 687 has two circumferential flanges 690, each dimensioned and configured to engage with two circumferential grooves 692 of nut 685. The engagement between post 687 and nut 685 is non-threaded, so that rotation of one does not necessarily cause rotation of the other. However, the axial position of both post 687 and nut 685 along barrel 621 is fixed. Since post 687 is not threaded, it can only be axially pushed along barrel 621, unless rotation of nut 685 and/or lag screw 650 causes axial movement of post 687 through the interface between post 687 and nut 685. At the proximal most end of post 687 is a non-circular recess 695 for engagement with a tool.

Flanges 690 are each eccentric and not fully circular, such that each defines a relief 694 as shown in FIG. 18. Relief 694 is a portion of flange 690 that coincides substantially with the outer dimension of proximal end 689. Relief 694 can be flat or curved around a portion of the periphery of post 687. While the number of flanges 690 can vary, the relief 694 of each flange 690 is aligned along the axis of post 687. In this way, when reliefs 694 are all oriented toward nut 685, there is no overlap in the dimensions between post 687 and nut

685 such that post 687 can slide along its axis without being axially linked with nut 685. Thus, lag screw 650 and nut 685 can be assembled prior to post 687, which can be oriented with reliefs 694 facing nut 685 and slid axially into position adjacent nut 685. In this position, use of a driver in the non-circular recess 695 can facilitate rotation of post 687 such that flanges 690 engage grooves 692 to axially link post 687 and nut 685. If after insertion of system 601 the fractured bone heals and compresses, nut 685, post 687, and lag screw 650 can all slide axially in a linked configuration within barrel 621.

While the embodiments and methods have been described in connection with a femur, use of the present embodiments with a humerus, a tibia, or any other bone is contemplated.

Each component of the aforementioned systems may be formed by an additive manufacturing process, including but not limited to electron beam melting (EBM), selective laser sintering (SLS), selective laser melting (SLM), binder jet printing, and blown powder fusion for use with metal powders. This is particularly beneficial as the silhouette of the figure-8 shape or other non-circular shape can be made with a specific patient's anatomy in mind, specifically to narrow, widen, lengthen, and/or shorten any of the dimensions of the system. Each component of the systems can be made of any surgical grade material, and particularly various metals such as titanium, titanium alloys, stainless steel, cobalt chrome alloys, tantalum and niobium, or any combination thereof. Gold and/or silver can be provided in the material composition or as a coating of a component. Systems can be used with other fixation components such as a retrograde nail as indicated above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fracture fixation system, comprising:

a fixation element including a plate and a barrel, the plate having an inner surface for placement against an exterior surface of a bone, and the barrel extending along a barrel axis and having a peripheral wall protruding from the inner surface of the plate, the fixation element defining a passage through the plate and the barrel that extends along the barrel axis, wherein at least a portion of an inner surface of the peripheral wall of the barrel has a figure-8 shape in a plane perpendicular to the barrel axis; and a monolithic peg extending along a peg axis and configured for insertion into the passage, wherein a body of the peg has an outer surface defining a figure-8 shape in a plane perpendicular to the peg axis.

2. The fracture fixation system of claim 1, wherein the peg is comprised of overlapped cylindrical portions that define the figure-8 shape of the outer surface of the peg.

3. The fracture fixation system of claim 2, wherein the overlapped cylindrical portions include a larger cylindrical portion defined by a larger radius and a smaller cylindrical portion defined by a smaller radius.

4. The fracture fixation system of claim 3, wherein each of the larger and smaller cylindrical portions of the peg defines a lumen.

5. The fracture fixation system of claim 4, wherein the lumen of the smaller cylindrical portion has a diameter that is larger than a diameter of the lumen of the larger cylindrical portion.

6. The fracture fixation system of claim 2, wherein the cylindrical portions of the peg have different maximum lengths along the peg axis.

7. The fracture fixation system of claim 3, wherein the larger and smaller cylindrical portions of the peg have different maximum lengths along the peg axis.

8. The fracture fixation system of claim 1, wherein a portion of the peripheral wall of the barrel defines a spring arm with a hook facing toward an internal space of the barrel.

9. The fracture fixation system of claim 8, wherein a groove of the peg in an outer surface of the peg and configured for engagement with the hook extends only along a portion of a length of the peg and defines an end wall, such that the hook limits movement of the peg within the passage when the hook contacts the end wall.

10. The fracture fixation system of claim 1, wherein separate portions of the peripheral wall of the barrel define respective first and second spring arms each having a hook.

11. The fracture fixation system of claim 10, wherein:

a first groove in an outer surface of the peg and configured for engagement with the first hook extends from a first end of the peg only along a portion of a length of the peg and defines a first end wall, such that the hook of the first arm limits movement of the peg within the passage when the first hook contacts the first end wall, and a second groove in the outer surface of the peg and configured for engagement with the second hook extends from a second end of the peg opposite the first end of the peg only along a portion of the length of the peg and defines a second end wall, such that the hook of the second arm limits movement of the peg within the passage when the second hook contacts the second end wall.

12. The fracture fixation system of claim 11, wherein the first end wall and the second end wall are misaligned along the peg axis.

13. The fracture fixation system of claim 11, wherein the second end of the peg is disposed closer to the plate than the first end of the peg when the peg is at least partially disposed within the passage of the fixation element, and wherein a floor of the second groove is tapered to be more shallow at the second end wall, and a floor of the first groove is at a substantially constant depth along an entire length of the first groove.

14. The fracture fixation system of claim 1, further comprising:

a threaded lag screw for insertion within a first lumen of the peg; and a threaded fixation screw for insertion through a screw hole at an end of the plate.

15. The fracture fixation system of claim 14, further comprising a positioning screw for insertion within a second lumen of the peg.

16. The fracture fixation system of claim 15, further comprising a collar having an outer surface for engagement with an inner surface of the second lumen of the peg, and an inner surface for engagement with a shaft of the positioning screw.

17. The fracture fixation system of claim 16, wherein the outer surface of the collar and the inner surface of the second lumen of the peg are non-circular, and the inner surface of the collar and the shaft of the positioning screw are threaded.

18. The fracture fixation system of claim 14, wherein the lag screw is comprised of distinct proximal and distal components that are assembled together within the first lumen.

19. The fracture fixation system of claim 1, wherein the fixation element is a single monolithic piece including the plate and the barrel.

20. The fracture fixation system of claim 1, wherein the plate and the barrel are separate distinct elements of the fixation element that are joined or connected together.

* * * * *